(12) United States Patent
Shkolnikov et al.

(10) Patent No.: US 10,444,155 B2
(45) Date of Patent: Oct. 15, 2019

(54) NANOSTRUCTURE WITH ELECTROWETTING

(71) Applicant: HEWLETT-PACKARD DEVELOPMENT COMPANY, L.P., Houston, TX (US)

(72) Inventors: Viktor Shkolnikov, Palo Alto, CA (US); Steven J Simske, Fort Collins, CO (US); Michael A Delos-Reyes, Corvallis, OR (US); Anita Rogacs, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 16/074,630

(22) PCT Filed: Oct. 10, 2016

(86) PCT No.: PCT/US2016/056306
§ 371 (c)(1),
(2) Date: Aug. 1, 2018

(87) PCT Pub. No.: WO2018/070989
PCT Pub. Date: Apr. 19, 2018

(65) Prior Publication Data
US 2019/0033219 A1   Jan. 31, 2019

(51) Int. Cl.
*B82B 1/00*  (2006.01)
*G01N 21/65*  (2006.01)
(Continued)

(52) U.S. Cl.
CPC ............ *G01N 21/658* (2013.01); *B82B 1/00* (2013.01); *G01J 3/44* (2013.01); *B82Y 30/00* (2013.01);
(Continued)

(58) Field of Classification Search
CPC ......... G01N 21/658; G01N 33/53; G01J 3/44; B82Y 30/00; G02B 2207/115; B01L 3/502761; B01L 2400/0427
See application file for complete search history.

(56) References Cited

U.S. PATENT DOCUMENTS

| 7,815,871 B2 | 10/2010 | Pamula et al. |
| 2002/0113961 A1* | 8/2002 | Gamble ................... G01J 3/44 |
| | | 356/301 |

(Continued)

FOREIGN PATENT DOCUMENTS

| CN | 102608103 A | 7/2012 |
| CN | 104849259 A | 8/2015 |

(Continued)

OTHER PUBLICATIONS

Barberoglou et al., "Electrowetting Properties of Micro/Nanostructured Black Silicon", American Chemical Society Retrieved from Internet—https://pubs.acs.org/doi/abs/10.1021/la101138u, 2010, 8 Pages.

(Continued)

*Primary Examiner* — Maurice C Smith
(74) *Attorney, Agent, or Firm* — Wall & Tong LLP

(57) ABSTRACT

An example device includes a substrate having a first surface, an electrowetting force generation layer above the first surface, and a nanostructure layer formed above the electrowetting force generation layer, the nanostructure layer having nano-fingers formed thereon. The electrowetting force generation layer is to generate an electrical field to selectively move at least one reactant on the nano-fingers of the nanostructure layer.

15 Claims, 5 Drawing Sheets

(51) Int. Cl.
    *G01J 3/44*     (2006.01)
    *B82Y 30/00*     (2011.01)
    *G01N 33/53*     (2006.01)

(52) U.S. Cl.
    CPC ........ *G01N 33/53* (2013.01); *G02B 2207/115* (2013.01)

(56) References Cited

U.S. PATENT DOCUMENTS

| | | |
|---|---|---|
| 2007/0070341 A1 | 3/2007 | Wang |
| 2014/0362373 A1 | 12/2014 | Lin et al. |
| 2015/0355097 A1* | 12/2015 | Zhou .................... G01N 21/658 506/13 |

FOREIGN PATENT DOCUMENTS

| | | |
|---|---|---|
| CN | 105772118 A | 7/2016 |
| CN | 105784670 A | 7/2016 |
| KR | 20140140886 A | 12/2014 |
| RU | 2543691 C2 | 3/2015 |

OTHER PUBLICATIONS

Moon et al., "Onchip Sample Preparation by Electrowettingondielectric Digital Microfluidics for Matrix Assisted Laser Desorption/Ionization Mass Spectrometry", Retrieved from Internet—https://ieeexplore.ieee.org/document/1454065, IEEE, 2005, 3 Pages.

* cited by examiner

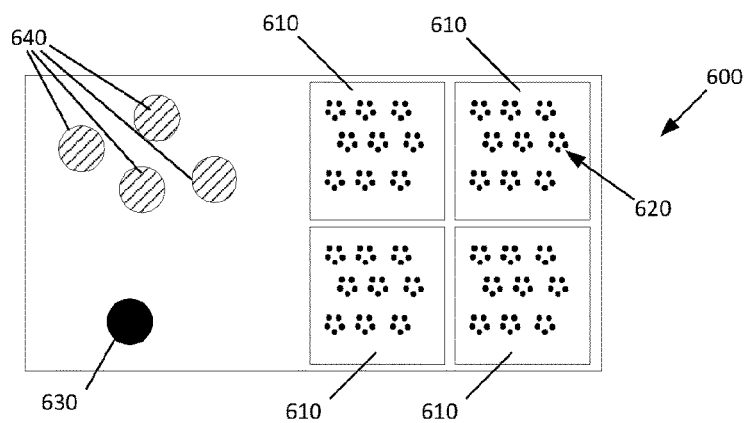
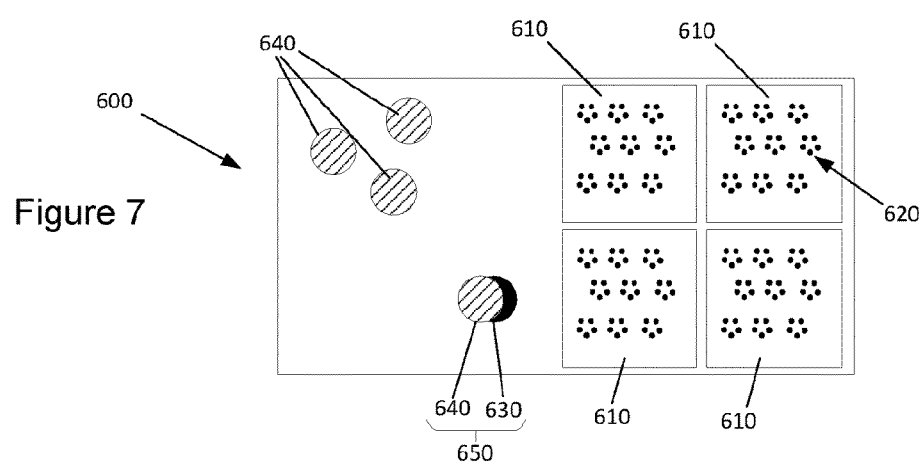
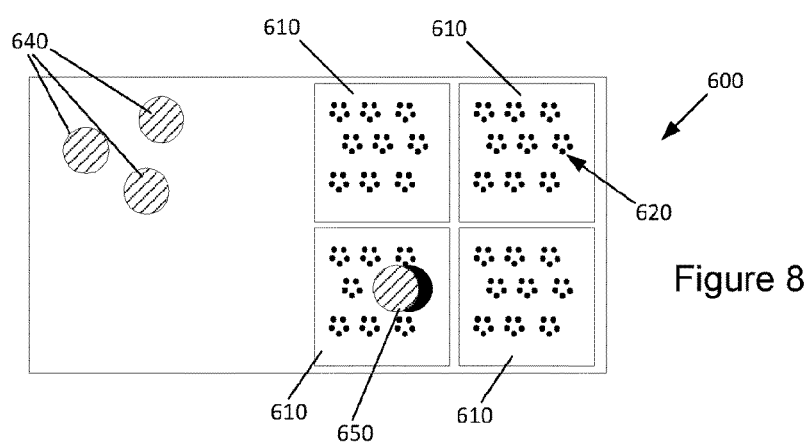

NANOSTRUCTURE WITH ELECTROWETTING

BACKGROUND

Surface-enhanced Raman Spectroscopy (SERS) is a sensitive technique which allows detection and identification of small amounts of a sample. For examples, single molecule sensitivity has been demonstrated. The sensitivity of SERS arises from enhancement of an electric field impinged on a molecule. SERS may be used for analysis of various materials, such as blood or other body fluids, for example.

BRIEF DESCRIPTION OF THE DRAWINGS

For a more complete understanding of various examples, reference is now made to the following descriptions taken in connection with the accompanying drawings in which:

FIGS. 6-8 illustrate different stages in an example preparation of a sample for sensing.

DETAILED DESCRIPTION

Various examples described herein provide for Surface-enhanced Raman Spectroscopy (SERS) with sample preparation and spectroscopy being performed on a single device. An example device includes a nanostructure layer with nano-fingers formed to facilitate spectroscopy of a sample with a Raman spectrometer. A layer provided below the nanostructure layer facilitates preparation of the sample on the nanostructure layer. In various examples, this layer includes patterned electrodes which can allow selective movement of various solution volumes, or reactants, onto a sensing region of the nanostructure layer.

As described above, SERS allows detection and identification of small amounts of a sample. However, samples such as milk, blood, plasma or saliva may contain various different molecules which may compete for access to the surface for enhancement of the Raman signal. Thus, samples often require preparation before analysis may be performed.

Figure 1:
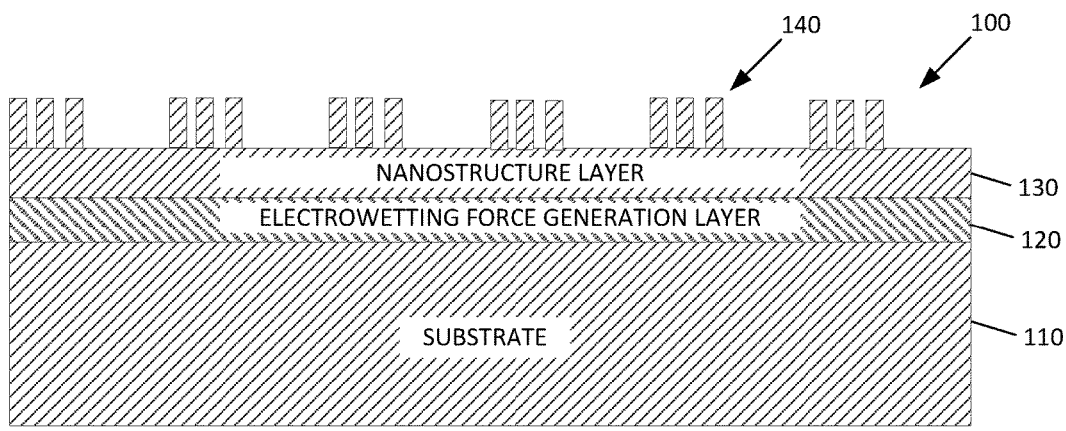
FIG. 1 illustrates a cross-sectional side view of an example device.

Referring now to FIG. 1, a cross-sectional view of an example device is illustrated. The example device 100 of FIG. 1 may be, for example, a lab-on-a-chip device or a part thereof. It will be understood that, for purposes of simplicity, FIG. 1 illustrates only a portion of the example device 100, which may include various other components.

The example device 100 includes a stack of layers which may be formed of a variety of materials. The example device 100 includes a substrate 110, which may be formed of a silicon material. In various examples, the substrate 110 may be formed of single crystalline silicon, polycrystalline silicon, gallium arsenide, glass, silica, ceramics or any semiconducting material. In one example, the substrate 110 has a thickness between about 500 μm and about 1200 μm. As used herein, "about" may include a value that is within ±10%.

An electrowetting force generation layer 120 may be formed on one surface of the substrate 110. In one example, the electrowetting force generation layer 120 includes patterned electrodes 222 that may be selectively actuated. The patterned electrodes 222 may be formed by depositing a conductive material, such as a metal (e.g., gold) or a reasonably conductive ceramic, through a shadow mask onto the substrate 110. The deposited patterned electrodes 222 may be covered with a non-conductive or dielectric material 224. In one example, the electrowetting force generation layer 120 may have a thickness between about 2 μm and about 100 μm.

The example device 100 of FIG. 1 includes a nanostructure layer 130 formed above the electrowetting force generation layer 120. The nanostructure layer 130 may be formed of a dielectric layer which may provide insulation of the patterned electrodes in the electrowetting force generation layer 120. In one example, the nanostructure layer 130 has a thickness of between about 2 μm and 100 μm.

In the illustrated example of FIG. 1, the nanostructure layer 130 has nano-fingers 140 formed thereon. The nano-fingers 140 extend upward from the nanostructure layer 130 and may be formed in clusters, as described in greater detail below. The dimensions of the nano-fingers 140 may be selected to provide sufficient flexibility to allow tips of the nano-fingers 140 to come together to trap molecules between the nano-fingers 140 to facilitate SERS.

The electrowetting force generation layer 120 may be provided to, when actuated, generate an electrical field to selectively move various solution volumes provided on the nanostructure layer 130. In one example, the patterned electrodes of the electrowetting force generation layer 120 may be selectively actuated to move the solution volumes to a desired location, such as a sensing area.

Figure 2:
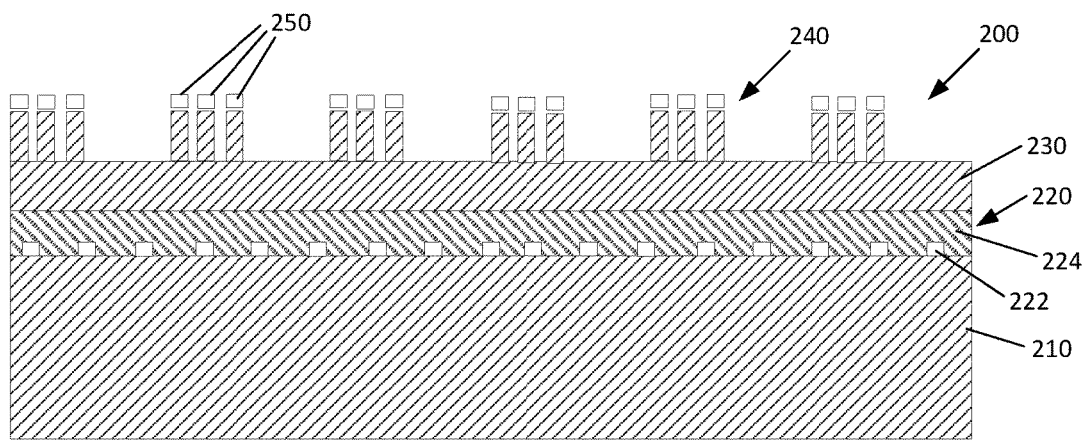
FIG. 2 illustrates a cross-sectional side view of another example device.

Referring now to FIG. 2, a cross-sectional view of another example device 200 is illustrated. The example device 200 of FIG. 2 is similar to the example device 100 of FIG. 1 and includes a substrate 210, an electrowetting force generation layer 220 and a nanostructure layer 230 with nano-fingers 240 formed thereon. In the example device 200 of FIG. 2, the nano-fingers 240 are provided with a coating 250 formed of a material selected to facilitate SERS analysis. In this regard, various nano-fingers 240 may be provided with the coating 250 formed of a material that facilitates hydrophobic interaction or hydrophilic interaction. In some examples, the coating 250 may be formed of a metal (e.g., a noble metal such as gold) to facilitate hydrophobicity, while in other examples, the coating 250 may be alcohol based to facilitate hydrophilicity.

Figure 3:
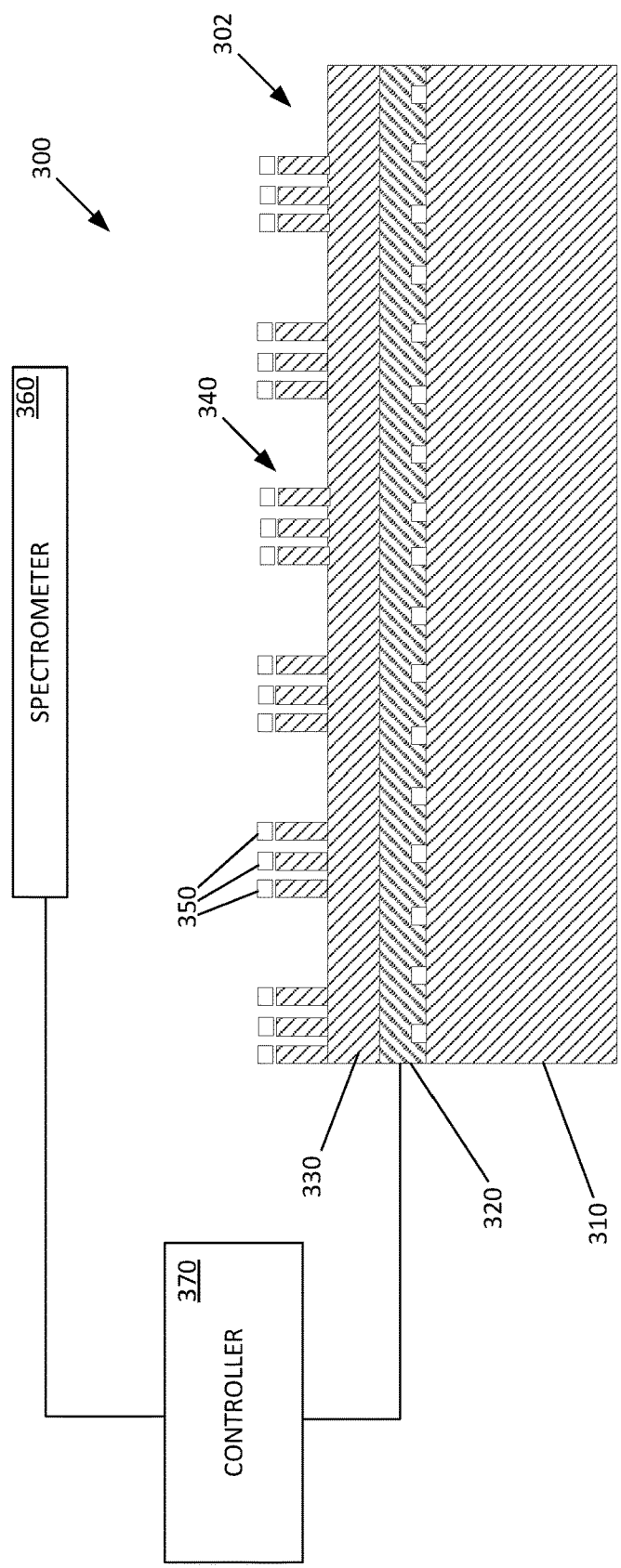
FIG. 3 illustrates an example system with the example device of FIG. 2.

Referring now to FIG. 3, an example system 300 is illustrated with an example device 302 that is similar to the example device 200 described above with reference to FIG. 2. Accordingly, the example device 302 includes a substrate 310, an electrowetting force generation layer 320 and a nano-finger layer 330 with nano-fingers 340 formed thereon. The nano-fingers 340 are provided with a coating 350 as described above. As noted above, the electrowetting force generation layer 320 may be a patterned electrode layer 320 with electrodes that may be selectively actuated.

The example system 300 of FIG. 3 is provided with a spectrometer 360 positioned above the nanostructure layer 330 of the example device 302. In one example, the spectrometer 360 is a Raman spectrometer. The spectrometer 360 may include a Raman signal generating light source, such as a laser, and a Raman signal detection portion to detect Raman scattered light signals for analysis.

The example system 300 further includes a controller 370 coupled to the spectrometer 360 and the example device 302. In particular, the controller 370 is coupled to the patterned electrode layer 320 to selectively actuate the various electrodes of the patterned electrode layer 320.

In this regard, the controller 370 may actuate the patterned electrode layer 320 to prepare a sample for analysis. As described in greater detail below with reference to FIGS. 6-8, the patterned electrode layer 320 may be used to move various solution volumes onto a sensing region of the nano-finger layer 330. The controller 370 may then activate the spectrometer 360 to analyze the sample in the sensing region of the nano-finger layer 330.

In various examples, the controller 370 may be a processor and may include an interface for receiving user instructions. In this regard, the controller may include or receive instructions to guide the operation of, for example, the patterned electrode layer 320. The controller 370 may further include the capability to perform analysis of Raman scattered light signals detected by the Raman signal detection portion of the spectrometer 360.

Figure 4:
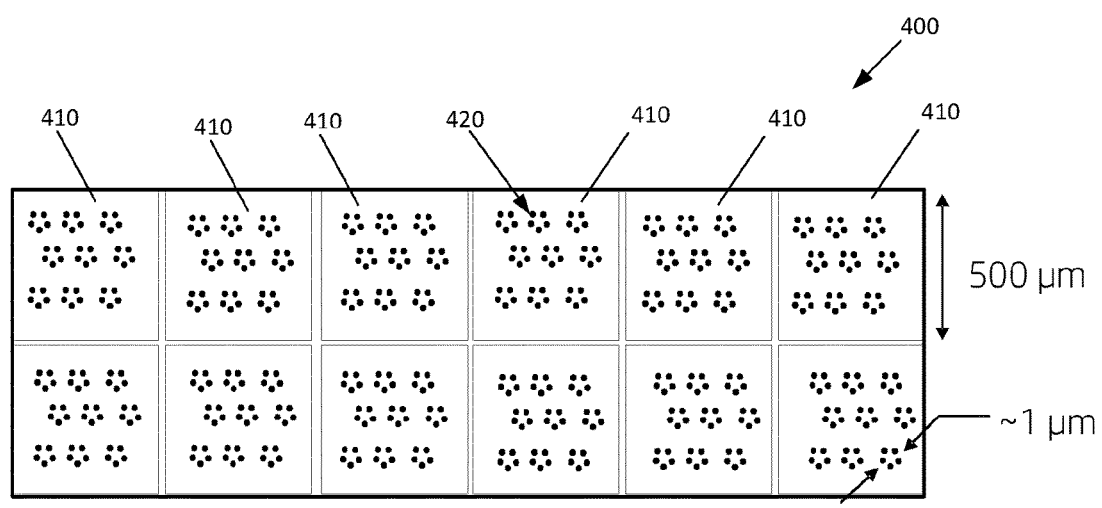
FIG. 4 illustrates a top view of an example device.
Figure 5:
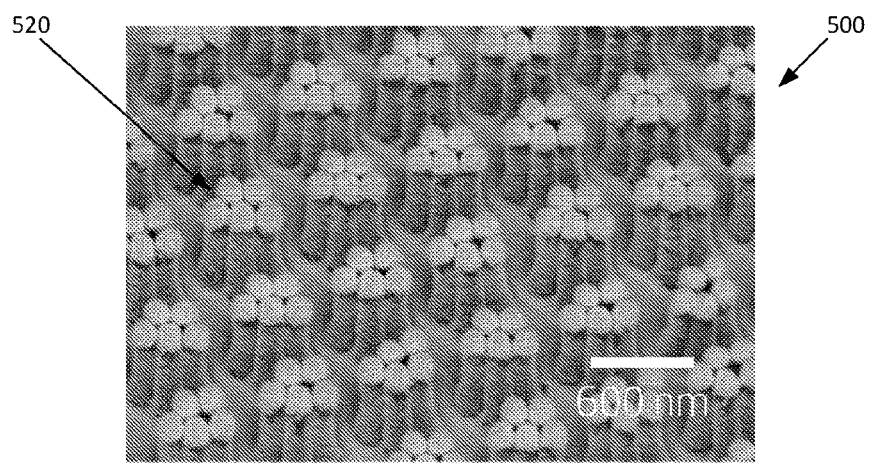
FIG. 5 illustrates an image of an example device with nano-fingers.

Referring now to FIG. 4, an example device 400 is illustrated in a top view. Further, an image of an example device 500 is illustrated in FIG. 5. The example device 400 and the example device 500 may be formed on a substrate (not shown). As shown in the top view of FIG. 4, a nanostructure layer is divided into a plurality of sensing regions 410. In the example of FIG. 4, the sensing regions 410 are arranged in a grid formation. In other examples, the sensing regions 410 may be arranged in various other configurations. Each sensing region 410 may be for analysis of a particular sample type, for example. Further, in the example of FIG. 4, each sensing region 410 has a square shape measuring about 500 µm on each side. In other examples, the sensing regions may have any of a variety of other shapes and sizes.

Each sensing region 410 is provided with at least one cluster 420 of nano-fingers. Clusters of nano-fingers 520 are also shown in the example device in the image of FIG. 5. In the example, of FIG. 4, each cluster 420 has a radius of approximately 1 µm and includes five nano-fingers. Of course, the number of non-fingers and the size of the cluster 420 may be varied as desired.

As described above, a patterned electrode layer may be provided below the nanostructure layer forming the grid of sensing regions 410. As described below with reference to FIGS. 6-8, various solution volumes may be moved to prepare a sample using the patterned electrode layer.

Referring now to FIGS. 6-8, an example process of preparing a sample is illustrated. FIGS. 6-8 illustrate an example device 600 with a grid of sensing regions 610 formed on a nanostructure layer. Each sensing region 610 is provided with a set of clusters 620 of non-fingers. In this regard, the example device 600 is similar to the example device 400 described above with reference to FIG. 4.

In the stage illustrated in FIG. 6, the example device 600 is provided with various solution volumes for the preparation of a sample for analysis. In the example of FIG. 6, the example device 600 is provided with a small amount of a sample 630 and at least one reagent 640. For the preparation of the sample 630 for analysis, the various solution volumes may need to be combined in, for example, a particular order. For example, in the example of FIGS. 6-8, the sample 630 may require combination with a reagent 640 prior to being moved to a sensing region 610.

Thus, as illustrated in FIG. 7, the patterned electrode layer may be actuated to move the sample 630 to a particular location. Subsequently, the patterned electrode layer may be actuated to move the reagent 640 to the same location for combining with the sample 630. In this regard, the sample 630 and the reagent 640 may combine in, for example, a chemical reaction to form an analyte 650 for analysis.

Referring now to FIG. 8, the patterned electrode layer may be used to move the analyte 650 to the desired sensing region 610. On the sensing region, the analyte may be captured by the cluster 620 of nano-fingers and prepared for SERS analysis.

The sample preparation process of FIGS. 6-8 is merely one example. In other examples, the sample 630 may be moved to a sensing region 610, and a solution volume 640 may then be moved to the sensing region 610 to form an analyte 650 at the sensing region 610. In other examples, the patterned electrode layer may be used to separate reagents to form an analyte 650.

Figure 9:
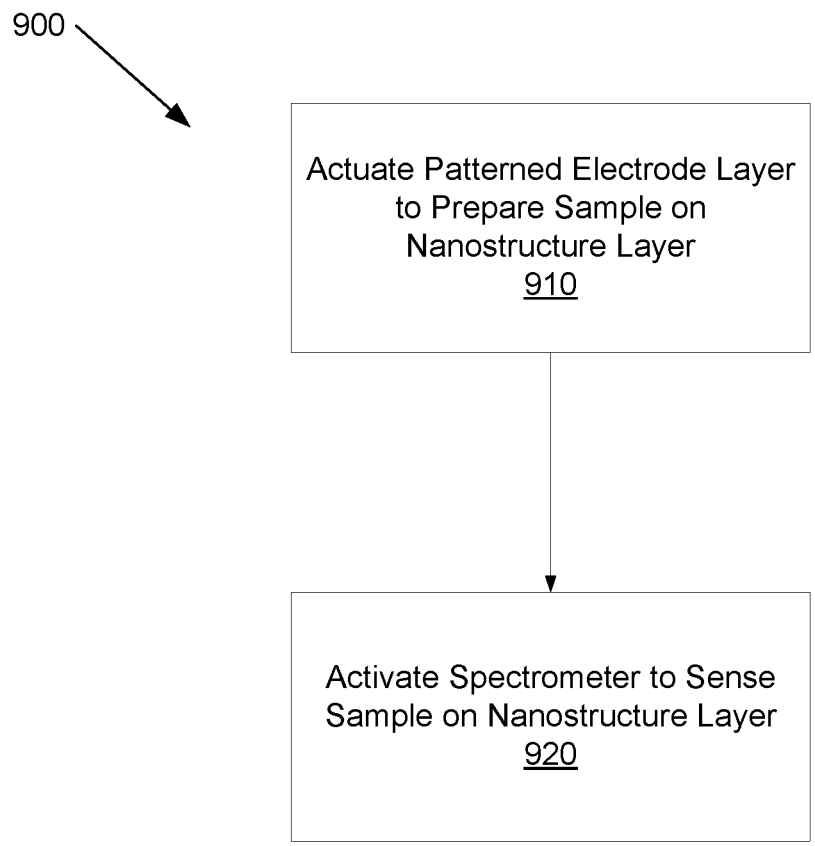
FIG. 9 illustrates an example process of analysis of a sample.

Referring now to FIG. 9, an example process 900 for analysis of a sample is illustrated. The example process 900 may be implemented in various components and systems. For example, the example process 900 may be implemented in the system 300 of FIG. 3 and, more particularly, in the controller 370 of the system 300. In accordance with the example process 900, a patterned electrode layer is actuated to prepare a sample on a nanostructure layer (block 910). For example, the patterned electrode layer 320 of FIG. 3 may be actuated by the controller 370 to prepare a sample in a sensing region of a nanostructure layer 330 formed above the patterned electrode layer 320. As described above with reference to FIG. 3, the nanostructure layer includes nano-fingers formed in the sensing region.

The example process 900 may further include activating a spectrometer to sense the sample on the nanostructure layer (block 920). For example, the controller 370 of the system 300 of FIG. 3 may activate a Raman spectrometer 360 positioned above the nanostructure layer 330 to analyze the sample in the sensing region of the nano-finger layer 370.

Thus, in accordance with various examples described herein, sample preparation and spectroscopy may be performed on a single device. An example device includes a nanostructure layer with nano-fingers formed to facilitate spectroscopy and a layer of patterned electrodes to facilitate preparation of the sample on the same nanostructure layer.

The various examples set forth herein are described in terms of example block diagrams, flow charts and other illustrations. Those skilled in the art will appreciate that the illustrated examples and their various alternatives can be implemented without confinement to the illustrated examples. For example, block diagrams and their accompanying description should not be construed as mandating a particular architecture or configuration.

What is claimed is:

1. A device, comprising:
   a semi-conductive substrate having a first surface;
   patterned electrodes formed by deposition of a conductive material onto the first surface of the semi-conductive substrate;
   an electrowetting force generation layer above the first surface and covering the patterned electrodes; and
   a nanostructure layer formed above the electrowetting force generation layer, the nanostructure layer having nano-fingers formed thereon, wherein the electrowetting force generation layer is to generate an electrical field with the patterned electrodes to selectively move at least one reactant on the nano-fingers of the nanostructure layer.

2. The device of claim 1, wherein nanostructure layer is formed of a dielectric.

3. The device of claim 1, further comprising a metal deposited on tips of at least some of the nano-fingers.

4. The device of claim 3, wherein the metal is a noble metal.

5. The device of claim 1, further comprising:
a Raman spectrometer positioned above the nanostructure layer, the Raman spectrometer including a light source to direct a light onto the nanostructure layer.

6. A system, comprising:
a nanostructure device having a patterned electrode layer deposited onto a first surface of a semi-conductive substrate, an electrowetting force generation layer above the first surface and covering the patterned electrodes, and a nano-finger layer formed above the patterned electrode layer and the electrowetting force generation layer;
a Raman spectrometer positioned above the nano-finger layer; and
a controller to:
actuate the patterned electrode layer of the nanostructure device to prepare a sample in a sensing region of the nano-finger layer; and
activate the Raman spectrometer to analyze the sample in the sensing region of the nano-finger layer.

7. The system of claim 6, wherein preparing of the sample includes selectively moving at least one solution volume into the sensing region.

8. The system of claim 7, wherein the preparing of the sample further includes combining at least two solution volumes in a specified order.

9. The system of claim 6, wherein activating the Raman spectrometer includes:
projecting a light onto the sensing region; and
analyzing reflected light from the sensing region.

10. The system of claim 9, wherein the light is a laser.

11. A method, comprising:
actuating a patterned electrode layer that is deposited onto a first surface of a semi-conductive substrate and covered by an electrowetting force generation layer above the first surface to prepare a sample in a sensing region of a nanostructure layer formed above the patterned electrode layer and the electrowetting force generation layer, the nanostructure layer having nano-fingers formed in the sensing region; and
activating a Raman spectrometer positioned above the nanostructure layer to analyze the sample in the sensing region of the nano-finger layer.

12. The method of claim 11, wherein preparing of the sample includes selectively moving at least one reactant into the sensing region.

13. The method of claim 11, wherein activating the Raman spectrometer includes:
projecting a light onto the sensing region; and
analyzing reflected light from the sensing region.

14. The device of claim 1, wherein a first subset of the nano-fingers are coated with a metal and a second subset of the nano-fingers are coated with an alcohol.

15. The method of claim 11, wherein the actuating comprises:
actuating a portion of the patterned electrode layer to move a reagent to a same location of the sample;
combining the sample and the reagent to form an analyte; and
actuating a second portion of the patterned electrode to move the analyte to the nano-fingers formed in the sensing region.

* * * * *